United States Patent [19]
Lin et al.

[11] Patent Number: 4,902,401
[45] Date of Patent: * Feb. 20, 1990

[54] DUAL GAS SENSOR HAVING SOLID ELECTROLYTE CONTAINED IN AN OXIDE MATRIX

[75] Inventors: Ching-Yu Lin, Monroeville; Richard P. Kunkle, Irwin, both of Pa.

[73] Assignee: Westinghouse Electric Corp., Pittsburgh, Pa.

[*] Notice: The portion of the term of this patent subsequent to May 9, 2006 has been disclaimed.

[21] Appl. No.: 301,412

[22] Filed: Jan. 25, 1989

[51] Int. Cl.$^4$ ............................................. G01N 27/46
[52] U.S. Cl. .................................... 204/427; 204/412; 204/424; 427/58; 427/431; 427/443.2
[58] Field of Search ..................... 204/1 S, 421–429; 429/16, 30–33, 46, 193

[56] References Cited
U.S. PATENT DOCUMENTS

| | | | |
|---|---|---|---|
| 3,120,456 | 2/1964 | Broers | 429/46 |
| 3,268,365 | 8/1966 | McQuade et al. | 429/16 |
| 3,915,830 | 10/1975 | Isenberg | 204/195 |
| 4,388,155 | 6/1983 | Chamberland et al. | 204/426 |
| 4,391,690 | 7/1983 | Lin et al. | 204/412 |
| 4,394,240 | 7/1983 | Pebler | 204/412 |
| 4,427,525 | 1/1984 | Lin et al. | 204/424 |
| 4,744,954 | 5/1988 | Campbell et al. | 204/421 |

Primary Examiner—T. Tung
Attorney, Agent, or Firm—Daniel P. Cillo

[57] ABSTRACT

A solid electrolyte dual gas sensor (10) is made, containing a container body of a first solid electrolyte (11), in contact with a monitor electrode (17) exposed to a monitored gas environment (13) containing selected gas components to be measured and in contact with a reference electrode (15) which is additionally isolated from the monitored gas environment by a second solid electrolyte section (16), and optionally section (14), where the solid electrolyte section (16) is disposed within a ceramic oxide matrix material (25) where the matrix contains interconnected pores filled with electrolyte, and where the second solid electrolyte, at the operating temperature of the gas sensor, is effective to dissociate to provide the sole source of self-generated reference gases at the reference electrode (15).

10 Claims, 3 Drawing Sheets

DUAL GAS SENSOR HAVING SOLID ELECTROLYTE CONTAINED IN AN OXIDE MATRIX

BACKGROUND OF THE INVENTION

1. Field of the Invention

This invention relates to unitary, self-generating reference gas sensors, useful to monitor not only a $SO_2$, $CO_2$ or $NO_2$ component, but also an $O_2$ gas component of a monitored gas environment.

2. Description of the Prior Art

The requirements for monitoring and controlling stack gas pollutants have resulted in the development of solid electrolyte gas sensors having electrolyte compositions uniquely responsive to gases such as $SO_2$, $CO_2$ and $NO_2$. These sensors are electrochemical concentration cells which sense the equilibrium of a gas species of interest and generate an EMF signal corresponding to the difference in partial pressure of the gas species across the solid electrolyte sensor. Typically, the solid state sensor includes an ion conductive solid electrolyte with electrodes disposed on its opposite surfaces. The stack gas, or monitored gas stream, contacts a sensing electrode, while the opposite electrode serves as a reference electrode which is contacted with a reference gas stream. Conventional solid electrolyte compositions require operating temperatures of between 200° C. and 900° C. to exhibit the desired ion conductivity to generate a suitable EMF signal.

In the past, a major problem with these devices was isolation of the monitored gas from the reference gas, to prevent unpredictable drift in the measurement signal. In an attempt to not only effectively seal monitored gas from the reference gas, but to also eliminate the effect of $O_2$ on the EMF signal measurement of $SO_2$, U.S. Pat. No. 4,391,690, (Lin et al.) taught construction of a dual gas monitoring sensor device. Different and separate sensor cells were described: an $SO_2$ cell having a $K_2SO_4$ solid electrolyte, which is fed a $SO_2$ reference gas stream, and is also connected to a source of $O_2$; and an $O_2$ cell having an oxygen ion conductive solid electrolyte, which is fed an air reference gas stream. This sensor design, however, is complicated to make and operate. Also, the use of a $SO_2+O_2$ reference gas stream, is inconvenient and expensive, since a constant supply of certified tank gas is needed.

Several instances of simplified, unitary gas sensors have been disclosed in the art. In U.S. Pat. No. 3,915,830, (Isenberg) relating to $O_2$ sensors, taught hermetically encapsulating a metal/metal oxide reference medium, such as nickel/nickel oxide, exhibiting a stable oxygen activity, within a small, stabilized zirconia solid electrolyte disc. U.S. Pat. No. 4,394,240, (Pebler) taught triangular, combination, multisensor electrochemical cells, which form an internal cavity which contains a common internal gas forming reference. In the triangular configuration, two sides were made of stabilized zirconia, oxygen ion conductive solid electrolyte and measure partial pressure of $O_2$, and the third side could be made of $K_2SO_4$ solid electrolyte when the partial pressure of $SO_3$ or $SO_2$ gases are to be measured. Reference electrodes were disposed on the inside electrolyte walls of the triangular configuration and sensing electrodes were disposed on the outside electrolyte walls.

The measuring concept in the Pebler patent utilized heating a central, enclosed, $MgSO_4$, $MnSO_4$ or $Ag_2SO_4$ reference material, which provides $SO_3$ on decomposition. This reference material had to be kept sealed from $K_2SO_4$ electrolyte, because of the possible reaction of these two components at high temperatures. Each of the three cells had its own circuitry. Two cells were exposed to flue gas, and one of the zirconia cells is exposed to an environment of known oxygen partial pressure, such as air.

In an attempt to provide a simple, inexpensive construction that would be effective to measure $SO_2$, $CO_2$ or $NO_2$ content of flue gases, U.S. Pat. No. 4,828,672 teaches a simplified, inexpensive, unitary, self-generating reference gas sensor. There, a reference electrode is isolated from the monitored gas environment by solid electrolyte, and the solid electrolyte itself, upon the application of heat, is effective to dissociate and provide the sole source of a self-generated gas, such as $SO_2+O_2$, $CO_2+O_2$, or $NO_2+O_2$ at the reference electrode. That design could measure only $SO_2+O_2$, $+CO_2$, or $NO_2+O_2$, so that a separate $O_2$ sensor would have to be installed along with the Lin et al. sensor, and the $O_2$ concentration, in terms of voltage output, would have to be compensated for electronically.

In an attempt to provide a self-referencing gas sensor useful to monitor not only a $SO_2$, $CO_2$ or $NO_2$ component, but also an $O_2$ gas component, U.S. Pat. No. 4,828,671 (Lin et al.) teaches a stabilized zirconia cup which contains a solid mass of $K_2SO_4$, $K_2CO_3$, or $KNO_3$, and the like electrolyte, where the zirconia is a $O_2$-cell and the $K_2SO_4$ was an $SO_2$-cell. An inner Pt-electrode is sealed in the zirconia cup and embedded in the electrolyte, and is used as a common reference electrode. The $K_2SO_4$ or like material is press-sintered at 100° C. below its melting point within the zirconia cup to provide a solid, fused, electrolyte mass. It was found, that upon cooling, the $K_2SO_4$ or like material could, in certain instances exhibit a large volume change during cooling to solidification which could lead to cracks in the electrolyte. What is needed is a further advanced design to provide a completely sealed, combined $SO_2$-/$O_2$, unitary, self-referencing gas sensor. It is one of the main objects of this invention to provide such a construction.

SUMMARY OF THE INVENTION

Accordingly, most generally, the invention resides in a solid electrolyte dual gas sensor for measuring two selected component gases of a monitored gas environment and containing first and second monitor electrodes in contact with the monitored gas environment and solid electrolyte, and a single reference electrode surrounded by a first solid electrolyte and a separate second solid electrolyte and being isolated from the monitored gas environment, where the first solid electrolyte is oxygen ion conductive, and the second solid electrolyte is sodium or potassium ion conductive and is adapted upon heating to dissociate and provide the sole source of reference gases at the reference electrode corresponding to the selected component gases to be measured in the monitored gas environment, characterized by the second solid electrolyte being a single component composition disposed within a ceramic oxide matrix material which contains interconnected pores filled with the electrolyte, allowing a continuous ionic conduction path through the second, solid electrolyte within the matrix.

The invention also resides in a solid electrolyte dual gas sensor for measuring two selected component gases of a monitored gas environment by generating electrical signals on the basis of a difference in the partial pressure between the two selected component gases of the monitored gas environment at first and second monitor electrodes in contact with the monitored gas environment and solid electrolyte, and the corresponding component reference gases at reference electrode means in contact with a reference gas environment and solid electrolyte; characterized by a single reference electrode surrounded by a first solid electrolyte and a separate second solid electrolyte and being isolated from the monitored gas environment, the reference electrode contacting both electrolytes, the first electrolyte being oxygen ion conductive, and the second electrolyte having a composition conductive to sodium or potassium ions, one monitor electrode contacting the first solid electrolyte and, the other monitor electrode contacting the second solid electrolyte, where the second solid electrolyte is a single component composition disposed within a ceramic oxide matrix material which is 60% to 95% porous prior to electrolyte impregnation, which matrix contains interconnected pores filled with electrolyte, allowing a continuous ionic conduction path through the second, solid electrolyte within the matrix, which second electrolyte is adapted upon heating to dissociate and provide the sole source of constant partial pressures of self-generated reference gases, at the reference electrode corresponding to the selected component gases to be measured in the monitored gas environment, to provide a unitary, dual gas sensor. The first electrolyte preferably acts as a containment vessel for a majority of the second electrolyte and oxide matrix.

The invention is further characterized in that the second electrolyte can be composed of an electrolyte impregnated matrix portion as described previously which is disposed next to a void free solid section, at least 95% dense, which contacts the monitored gas environment and supports a metal monitor electrode. This latter section can overlap the edges of the first electrolyte container, to ensure that there is no gas leakage to the interior reference electrode which is in contact with the reference gas environment. Monitor electrode means contact the outer surface of both electrolytes. This provides a unitary, dual gas sensor apparatus, where the combination of solid electrolytes is effective to prevent monitored gas contact with the reference electrode means. Also included are measuring circuit means connected to all the electrodes of the sensor, which is effective to generate electrical signals to measure the selected gas components in the monitored gas environment.

Further, according to the invention is a method of making the gas sensor characterized by the steps of: disposing a 35% to 95% porous ceramic oxide matrix, containing interconnected pores, into a closed end tube comprising zirconia, on top of a metal reference electrode having a metal lead passing through the closed end of the tube; impregnating the porous ceramic oxide matrix with molten electrolyte selected from one of the group consisting of $K_2SO_4$, $Na_2SO_4$, $K_2CO_3$, $Na_2CO_3$, $KNO_3$ and $NaNO_3$, to provide an electrolyte containing assembly; cooling the assembly to provide electrolyte disposed within the interconnected pores of the matrix, allowing a continuous ionic conduction path through the electrolyte within the matrix; adhering a dense, additional electrolyte section of the same composition as the electrolyte in the matrix on top of the impregnated matrix and tube; and attaching an exterior reference electrode to the top of the dense, additional electrolyte section, and to the zirconia closed end tube.

This dual gas sensor eliminates the need to supply any separate reference gas stream in the reference system, its impregnated matrix electrolyte structure eliminates possibilities of cracks, the gas sensor can be miniaturized, and its manufacture and operation can provide substantial cost savings. This sensor is effective within the temperature range of 200° C. to 900° C.

BRIEF DESCRIPTION OF THE DRAWINGS

In order that the invention can be more clearly understood, convenient embodiments thereof will now be described, by way of example, with reference to the accompanying drawings in which.

DESCRIPTION OF THE PREFERRED EMBODIMENTS

Figure 1:
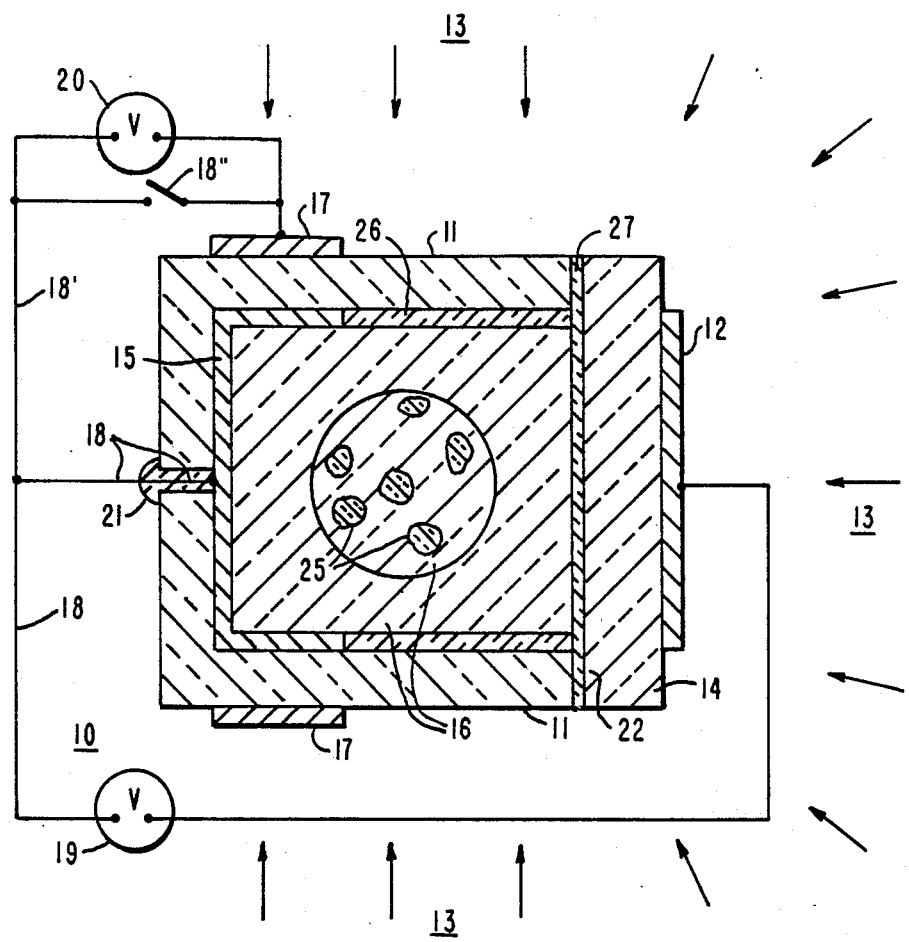
FIG. 1 is a cross-sectional view of one embodiment of a unitary, self-generating reference gas, dual sensor of this invention, showing an enlarged, idealized matrix-solid electrolyte portion.

Referring now to FIG. 1, solid electrolyte, unitary, dual gas sensor electrochemical cell 10 is shown. This dual gas sensor cell is preferably contained within a non-porous, high temperature stable, gas impermeable vessel 11. Yhis vessel is usually a dense ceramic cylindrical cup or bored out tube made of a material that conducts oxygen ions at relatively high temperatures, such as stabilized zirconia, which acts as a first solid electrolyte for the sensor. The preferred first electrolyte 11 is stabilized zirconia, preferably $ZrO_2$ doped with a minor amount, usually from 5 atom percent to 15 atom percent, of yttrium oxide, $Y_2O_3$. Calcia, CaO, can also be used as a dopant. This solid electrolyte container or vessel 11 would be isostatically pressed at high temperatures, to provide a sintered, high density (at least 90% dense) cup or tube.

A first, metal, monitor electrode means 12, preferably platinum, is in contact with the monitored gas environment 13, shown by arrows, containing the gas components to be measured, and a void-free, second solid oxide electrolyte for the sensor. The second solid electrolyte optionally, can be divided into highly densified solid electrolyte section 14, which contacts the metal, monitor electrode means 12, and solid electrolyte section 16 which is contained within a highly porous matrix 25, shown in the enlarged portion of FIG. 1, which electrolyte section 16 contacts the metal, reference electrode means 15 of the sensor. This reference electrode is preferably a single, common, platinum electrode structure.

The second electrolyte sections 14 and 16 would both be made of a material which, at high temperatures, is effective to conduct ions selected from one of the group consisting of sodium ions and potassium ions. Sections 14 and 16 would both be made of the same material. Electrolyte body 14 is a single member, such as a disc, that can be isostatically pressed at high temperature and pressure to over 98% of theoretical density. In the broadest embodiment of the invention, the electrolyte section 14 will not be used, and the second solid electrolyte will all be contained within a ceramic oxide structure.

In the preferred embodiment, electrolyte section 16, when initially formed, extends somewhat beyond the vessel top, so that when electrolyte section 14 is pressed against section 16 a good contact is established and ionic conductivity is not hindered at the interface of the two. Also, electrolyte section 14 overlaps the edges of the first electrolyte containment vessel 11 at 22, to insure that there is no gas leakage of monitored gas environment 13 to the interior reference electrode 15. Second, metal, monitor electrode means 17 is on the outside of electrolyte vessel 11, preferably as a continuous band of platinum wire. Thus, both monitor electrodes 12 and 17 contact the monitored gas environment 13. First monitor electrode 12 also contacts electrolyte body 14, and second monitor electrode 17 also contacts electrolyte body 11 in the form of a containing vessel. Also, as shown, the electrolytes contact the monitored gas environment.

The solid electrolyte in sections 14 and 16 will preferably be at least 95% dense, and will be of at least 95% purity. The solid electrolyte 11, and the solid electrolyte in sections 14, and 16 will initially constitute submicron particles, preferably in a range from approximately 0.1 micrometer to 0.9 micrometer, and will be effective to prevent monitored gas 13 contact with the reference electrode means 15. Solid electrolyte particles for electrolyte 11 and electrolyte section 14 will be press sintered into form. Solid electrolyte particles for electrolyte section 16 will be melted and vacuum impregnated into matrix 25 in molten form to permeate all the matrix pores, and then allowed to cool, as described hereinafter. The preferred material for all the electrodes as well as electrical leads 18, is platinum.

The second solid electrolyte section 16 consists of 65% to 95% by volume solid electrolyte which conducts sodium or potassium ions and 5% to 35% by volume of high temperature stable ceramic oxide matrix, shown as 25 in FIG. 1. The matrix is 35% to 95% porous prior to electrolyte inclusion. This matrix 25 preferably contains small pores having approximate diameters of up to 150 micrometers, preferably from 0.1 micrometer to 100 micrometers which are filled with solid electrolyte 16, allowing a continuous ionic conduction path through the solid electrolyte 16 in the matrix 25. The matrix will constitute a foam or sponge like, interconnected skeletal structure having a large void volume and large surface areas. Useful materials for the high melting ceramic oxide matrix material 25 are selected from the group consisting of quartz ($SiO_2$ m.p. 1,710° C.), alumina ($Al_2O_3$ m.p. 2,030° C.), zirconia ($ZrO_2$ m.p. 2,700° C.), magnesia (MgO m.p. 2,800° C.), mullite ($3Al_2O_3.2SiO_2$ m.p. 1,810° C.), and other ceramic oxides having a melting point greater than 1,600° C., in the form of a frit disc made from finely powdered particles. The preferred porosity of matrix 25 is from 50% to 90% porous. Porosity below 35%, pores may not be continuous. Porosity over 95%, the matrix itself may crumble or crack as the impregnated electrolyte solidifies.

Useful electrolyte materials 16 include $K_2SO_4$ (m.p. 1,072° C.), $Na_2SO_4$ (m.p. 888° C.), $K_2CO_3$ (m.p. 891° C.), $Na_2CO_3$ (m.p. 109° C.), KNO (m.p. 300° C.) and $NaNO_3$ (m.p. 308° C.), all of which have a low viscosity in the molten state. The preferred electrolytes are $K_2SO_4$ and $Na_2SO_4$. With the combination of the low viscosity of the molten impregnants and the relatively large surface area of the porous matrix substrate, the molten electrolyte is easily absorbed in the porous ceramic substrate and remains there after the electrolyte solidifies during the cooling process. Because of the small pore size in the ceramic matrix, cracking in the solidified electrolyte due to thermal shock is minimized. Because the pores in the substrate are continuous, the solidified electrolyte contained in the ceramic matrix is also a continuous phase, which provides an ionic conduction path between electrodes. These impregnants, in the molten state, will be drawn into the pores of the ceramic oxide matrix by capillary action. Also shown in FIG. 1 is an optional bonding layer 27 of fine eutectic $Na_2SO_4$-$K_2SO_4$ powder or $K_2SO_4$ powder having a particle size of from 0.05 micrometer to 1.0 micrometer, that can be used in the optional, dual second solid electrolyte structure.

Measuring circuit means, comprising electrical lead wires 18 and 18' are connected to the electrode means 12 and 15, and 15 and 17 respectively, to establish two circuits. The circuit means are also connected to voltmeters 19, used for $SO_2$, and 20, used for $O_2$ as shown. These circuits respond to electrical signals generated in the sensor. These circuits provide an indication of both the partial pressures of selected gas components in the monitored gas environment to be measured, and the partial pressures of the corresponding similar gases generated by decomposition of the second electrolyte bodies 16 and 14, as described hereinafter.

A high temperature stable, ceramic oxide sealant 21, such as, for example, a mixture of 49 mole % $La_2O_3$ and 51 mole % $AL_2O_3$ powders, having a melting point of approximately 1,710° C., can be applied and melted in place to ensure isolation of monitor electrode means 15. High temperature ceramic cement filler 26 which optionally can be disposed between the electrolyte materials 11 and 16 is also shown. Cement filler 26 can be painted and dried on the inside of tubular electrode 11. Useful cement fillers are high temperature alumina based cements in a fugitive bonder and the like which can be cured at from about 800° C. to 900° C. A ceramic spacer and a spring means, neither shown in FIG. 1, can be used respectively to protect body 14 and to insure good electronic contact between bodies 14 and 16. The main body of this dual gas sensor can be inserted or assembled into a probe structure, having a heating element and temperature control, to provide a gas-sensing apparatus.

The EMF (electromotive force) signals generated by the solid electrolyte dual gas sensor cell, are developed in accordance with the well-known Nernst equation, where the variables include the cell temperature, and the variation of partial pressure of the gas components of interest in the monitored gas environment at the monitor electrodes 12 and 17, and the partial pressure of the same reference gases at the common reference electrode 15. In this invention, the solid second electrolyte itself is a self-reference electrolyte, which upon the application of heat, is effective to dissociate, to provide the sole source of reference gases.

In the case where the monitored gas environment contains $SO_2$ and $O_2$, two gas components to be measured, and where the solid electrolytes are $K_2SO_4$, 16 and optional 14 for the $SO_2$ cell portion of the sensor, and stabilized zirconia, 11, for the $O_2$ cell portion of the sensor; upon operation of the sensor cell at from 600° C. to 900° C., the $K_2SO_4$ solid electrolyte will be in equilibrium dissociation to provide a $SO_2+O_2$ reference gas, according to the chemical reaction:

$$K_2SO_4 \rightleftharpoons 2K^+ + SO_2 + O_2.$$

The cell assemblies will be:

$SO_2+O_2$ Reference Gas, $Pt|K_2SO_4|Pt$, $SO_2+O_2$ Flue gas, and $SO_2+O_2$ Reference Gas, $Pt|ZrO_2.Y_2O_3|Pt$, $SO_2+O_2$ Flue gas.

In this case, the EMF would be calculated from the equation:

$$EMF = \frac{RT}{2F} \ln \frac{P_{SO_2} \cdot P_{O_2}}{P'_{SO_2} \cdot P'_{O_2}}, \text{ for the } SO_2 \text{ cell, and}$$

$$EMF = \frac{RT}{4F} \ln \frac{P_{O_2}}{P'_{O_2}}, \text{ for the } O_2 \text{ cell,}$$

where R=the universal gas constant, T=temperature °K., F=Faraday Constant (23,061 cal./volt), P=partial pressure of reference gas, and P'=partial pressure of monitored gas, where R, T, F, and P are known. In the $SO_2$ cell, there are two electrons transfering and for the $O_2$ cell, there are four electrons transferring. From these equations, a direct measurement of $SO_2$ and $O_2$ component gases in the monitored gas environment can be made by the measurement of the EMF of the sensor cells.

Since the zirconia cell and the $K_2SO_4$ cell share a common inner reference electrode 15, the sensor is not only able to monitor $SO_2$ and $O_2$ separately, but also is capable of monitoring $SO_2$ directly in the flue gas independent of $O_2$ levels by shorting the sensing and reference electrodes of the zirconia cell; this provides an equal $O_2$ potential between the inner electrode and ambient.

For example, on open circuit, as shown in FIG. 1, voltmeter 19 will read: $SO_2$ concentration in terms of mV.$+O_2$ concentration in terms of mV., at an approximately 100 mV./decade concentration slope (slope of the calibration curve for $SO_2+O_2$). Voltmeter 20 will read $O_2$ concentration in terms of mV., at approximately 54 mV./decade concentration slope (slope of the calibration curve for $O_2$ alone). To get the concentration of $SO_2$ from a calibration curve, the following equation is used:

$EMF_{SO_2} = [(EMF_{SO_2} + EMF_{O_2})$ from voltmeter 19]$-[2EMF_{O_2}$ from voltmeter 20].

The ppm. $SO_2$ concentration is then read from the calibration curve, knowing $EMF_{SO_2}$. If the circuit 18' is shorted, for example switch 18" is thrown to close the circuit, the oxygen concentration across the first electrolyte 11 will equalize, providing an equal oxygen potential between the inner electrode and ambient. This is caused because $O_2$ will be pumped from the monitored gas environment, converted to oxygen ions, and then back to $O_2$ within the $K_2SO_4$ electrolyte. In this case, voltmeter 19 will read $EMF_{SO_2}$ alone, since $EMF_{O_2}=0$, by the equation:

$EMF_{SO_2} = [EMF_{SO_2} + O] - [O].$

When the selected gas component to be monitored is $SO_2$, the second solid electrolyte 16 and optional 14 will be selected from $K_2SO_4$ and $Na_2SO_4$. At 600° C. to 900° C. sensor operation, solid $K_2SO_4$ will be in equilibrium dissociation with $2K^+ + SO_2 + O_2$. At 600° C. to 780° C. sensor operation, solid $Na_2SO_4$ will be in equilibrium dissociation with $2Na^+ + SO_2 + O_2$. When the selected gas component to be monitored is $CO_2$, the solid electrolyte 16 and optional 14 will be selected from $K_2CO_3$ and $Na_2CO_3$. At 600° C. to 780° C. sensor operation solid $K_2CO_3$ will be in equilibrium dissociation with $2K^+ + CO_2 + \frac{1}{2}O_2$ and solid $Na_2CO_3$ will be in equilibrium dissociation with $2Na^+ + CO_2 + \frac{1}{2}O_2$. When the selected gas component to be monitored is $NO_2$, the solid electrolyte 16 and optional 14 will be selected from $KNO_3$ and $NaNO_3$. At 200° C. to 300° C. sensor operation, solid $KNO_3$ will be in equilibrium dissociation with $K^+ + NO_2 + \frac{1}{2}O_2$ and solid $NaNO_3$ will be in equilibrium dissociation with $Na^+ + NO_2 + \frac{1}{2}O_2$. This last sensor can be operated only at low or cooled flue gas temperatures, and must utilize a thin wall first electrolyte structure 11.

In all instances, at the operating temperature of the sensor cell, the self-reference second solid electrolyte, 16 and optional 14, itself provides the sole source of $O_2$, $SO_2$, $CO_2$ or $NO_2$ reference gas, depending on the solid electrolyte 14 and 16 used. The amount of $SO_2$, $CO_2$ or $NO_2$ generated by equilibrium dissociation of the second solid electrolyte 16 and optional 14 will be on the order of 0.5 ppm (parts per million) to 100 ppm, whereas the amount of $SO_2$, $CO_2$ or $NO_2$ in the monitored gas environment may be from 50 ppm to 2500 ppm, in most cases. There is no separate, exterior reference gas stream associated with this sensor apparatus. The only useful cations in the second solid electrolyte 16 and optional 14 are $K^+$ and $Na^+$, as they provide the best combination of low electrolyte resistance and highest decomposition temperature for the anions used.

Ideally, the partial pressure of $SO_2$ and $O_2$ or the other dissociation gas species at the reference electrode means 15, would be equivalent to the true dissociation pressure of $K_2SO_4$, or the other useful solid electrolytes described hereinbefore, at a controlled temperature, if the reference electrode is perfectly sealed in the second solid electrolyte section 16 without formation of any minute voids. Presence of minute voids in solid electrolyte section 16 could trap a variety of gas species during the electrolyte fabrication process, and could also accumulate $SO_2$ and $O_2$ gases from the dissociation reaction of solid electrolyte during sensor cell operation. The preferred solid electrolyte section 16 in this invention will be substantially free of minute voids. Vacuum impregnation of molten electrolyte powder into the ceramic oxide matrix will control void formation. Electrolyte section 16, after vacuum impregnation into the matrix structure, and solidification, will preferably be at least from 95% dense. Solid electrolyte sections 14 and 16 and electrolyte vessel 11 will preferably be at least 98% dense.

Since any voids present in the solid electrolyte section 16 would be minute under presently used powder sintering and vacuum impregnation techniques, and they would be either hermetically sealed or confined in a small space, these trapped gas species would tend to be in equilibrium with the solid electrolyte at a controlled temperature. Therefore, a stable and constant partial pressure of $SO_2+O_2$, or $CO_2+O_2$, or $NO_2+O_2$ is expected to be maintained at the reference electrode means 15, which would result in a stable and reproducible EMF measurement. What is essential is to establish a constant partial pressure of $SO_2+O_2$, or $CO_2+O_2$, or $NO_2+O_2$ at the reference electrode means 15 during sensor cell operation.

The invention will now be illustrated by the following EXAMPLE.

EXAMPLE

A double cell, self-generating referencing, combined, dual gas sensor, similar to that shown in FIG. 1, was made. A high purity (99+%) yttria doped zirconia $(ZrO_2)_{0.9}(Y_2O_3)_{0.1}$, closed end tube, approximately 1.5 cm long, 1.1 cm outside diameter, 0.9 cm inside diameter, and 0.2 cm thick, isostatically pressed to 98% density, was drilled at the middle of the closed end to provide a small hole about 1 mm. in diameter. This provided a first electrolyte in the form of a container vessel. Platinum wire was inserted through the hole, wound as a support, and soldered to a platinum electrode screen having a diameter of approximately 0.8 cm, held in place against the bottom of the tube. The platinum wire was sealed as shown in FIG. 1 by an adhesive mixture of 49 mole % $La_2O_3$ and 51 mole % $Al_2O_3$, which was melted at approximately 1,700° C. and allowed to cool and solidify to provide a vacuum tight seal.

A 99.9% pure, quartz ($SiO_2$) frit disc, approximately 0.8 cm in diameter and approximately 1.3 cm long, having a 90% porosity (10% of theoretical density) was painted with a viscous slurry of alumina ceramic cement in a fugitive binder. This same alumina ceramic cement was also painted on the inside wall of the closed end tube. Then the frit disc was inserted inside the closed end tube and the cement allowed to dry at 25° C. The closed end tube with inserted center frit disc was heated at 700° C. to cure the ceramic cement, providing a 98% dense outer cup containing a bonded, 90% porous, center, quartz frit matrix. Additional cement was then applied to the top edge of the porous quartz matrix to eliminate any gaps remaining around the cup wall.

The cup with its porous quartz frit center was then placed in a tubular quartz reactor furnace fitted for drawing a vacuum. Then, several pressed and sintered 90% dense $K_2SO_4$ discs approximately 0.9 cm in diameter were placed on top of the porous, quartz frit matrix center. A vacuum was drawn to eliminate air from the porous, quartz frit matrix and then the unit was heated to 1,100° C., about 40° C. over the melting point of the $K_2SO_4$ discs. After approximately 30 minutes all the $K_2SO_4$ melted and was drawn by capillary action into the pores of the quartz frit matrix. Knowing the volume occupied by the matrix and its porosity, an excess of $K_2SO_4$ was used so that some $K_2SO_4$ overflowed onto the dense closed end cup. The $K_2SO_4$ impregnated sensor was then cooled to 25° C. and excess $K_2SO_4$ carefully removed from the top and sides. Close examination of the surface did not show any evidence of cracking. A thin layer of $K_2SO_4$ powder, having a particle size of approximately 0.5 micrometer, was placed as a bonding layer on top of the $K_2SO_4$ impregnated matrix and top cup surface.

A specially densified disc, about 99% dense, of 99% pure, was then pressed and sintered onto the end of the zirconia vessel, into intimate contact with the $K_2SO_4$ powder bonding layer. A first, exterior, platinum monitor electrode screen was then pressed and bonded to the top of the outer $K_2SO_4$ densified electrolyte disc. A second, exterior, platinum monitor electrode, in the form of contacting wound wire, was wrapped around the bottom of the zirconia vessel. Platinum wire was then attached to the monitor electrodes. Wire leads from the two monitor electrodes and encapsulated interior sensing electrode were connected to two Keithley digital voltmeters in the circuit shown in FIG. 1. A ceramic spacer was placed over the exterior, platinum monitor electrode which was bonded to the $K_2SO_4$ disc and the whole sensor unit was installed into the cell-holder with a spring loading system, in a probe structure having a heating element and temperature control. Finally, the probe was heated to 1,040° C. so that the sulfates of the $K_2SO_4$ powder bonding layer form a semi-liquid state which when cooled "glues" the top densified $K_2SO_4$ disc onto the impregnated porous matrix and top cup surface, to provide a $SO_2/O_2$ gas sensor apparatus.

Figure 2:
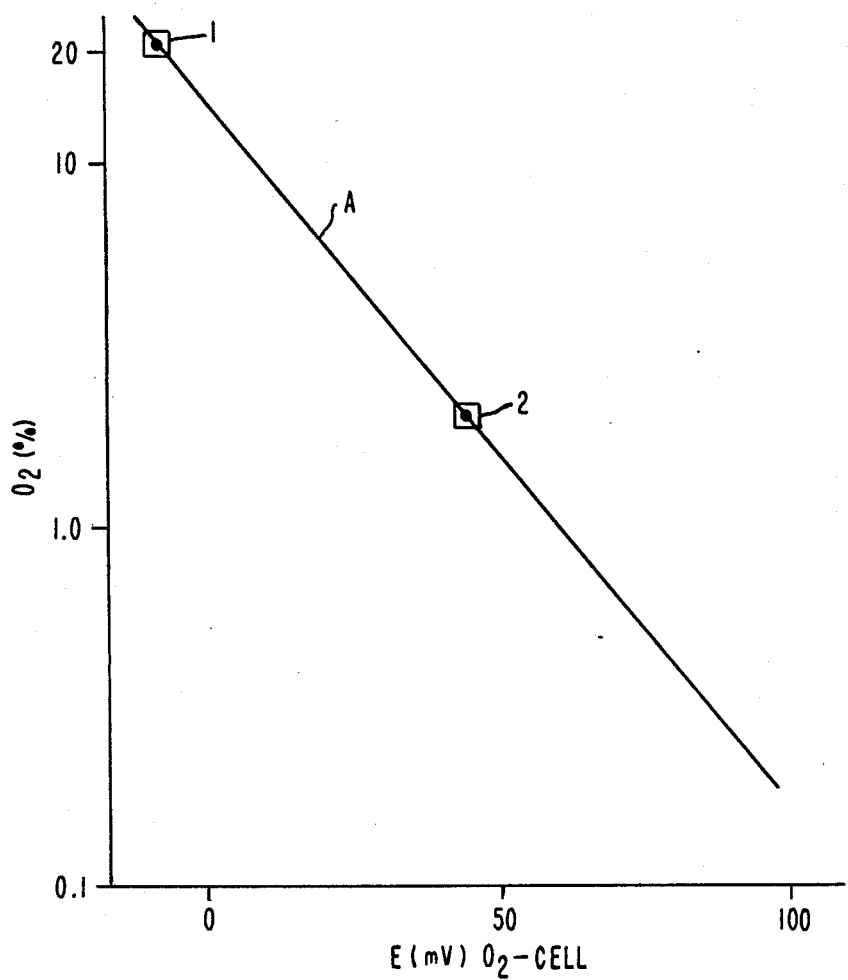
FIG. 2 shows an $O_2$ calibration curve at 855° C., of EMF vs. $\%O_2$ for the dual reference gas sensor of this invention.

This $SO_2/O_2$ gas sensor apparatus was tested at 855° C. FIG. 2 shows the $O_2$ calibration of the $O_2$ cell as Curve A in terms of % $O_2$ vs. EMF (mV). Data points are shown on Curve A. Point 1 shows a reading of −4 mV for 21% $O_2$ in nitrogen, and point 2 shows a reading of 45 mV for 2% $O_2$ in nitrogen. The slope of Curve A is about 54 mV per decade of $O_2$ concentration. The term "decade" concentration means, for example, on a log scale, 1 ppm to 10 ppm, or 10 ppm to 100 ppm, or 100 ppm to 1,000 ppm, etc., as shown in FIG. 2.

Figure 3:
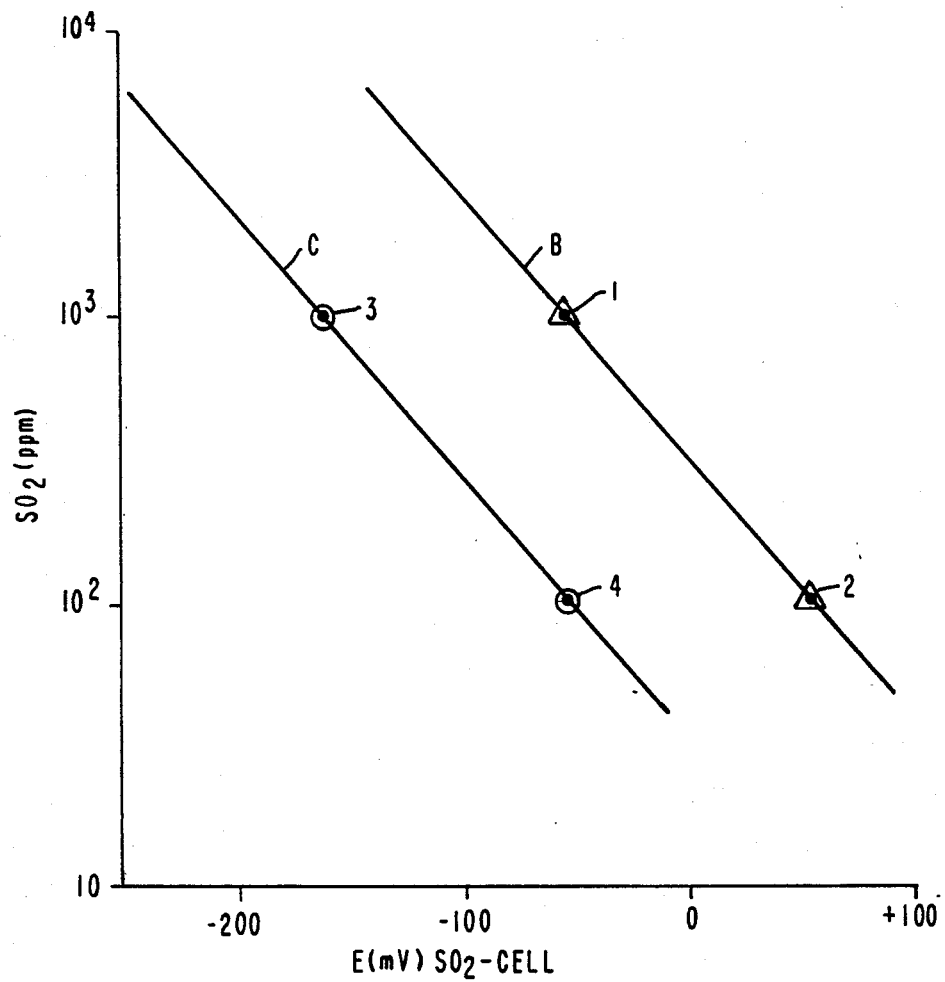
FIG. 3 shows an $SO_2+O_2$ calibration curve at 855° C., of EMF vs. ppm $SO_2$, for the dual reference gas sensor of this invention.

The $SO_2+O_2$ calibration curves of the $K_2SO_4$ cell in the sensor are shown in FIG. 3, as Curves B and C. Curve B shows a point 1 reading of −50 mV from 1,000 ppm $SO_2$ in 2% $O_2$ with the balance $N_2$, and a 55 mV reading for 100 ppm $SO_2$ in 2% $O_2$, with the balance $N_2$, point 2. Curve B has a slope of 108 mV per decade of SO concentration. Curve C, point 3 shows a reading of −165 mV for 1,000 ppm $SO_2$ in air, i.e., in 21% $O_2$ with the rest $N_2$ and a point 4 reading of −50 mV for 100 ppm $SO_2$ in air. Curve C also has a slope of 108 mV/decade. The difference in mV between Curves B and C was 107 mV.

These test results revealed that both the zirconia cell and the $K_2SO_4$ cell of the sensor responded to $O_2$ and to $SO_2+O_2$ fairly well in agreement with the prediction of the Nernst equations. The reproducibility of the sensor apparatus to different $SO_2$ and $O_2$ levels was very good.

Since the partial pressure of total reference gas, i.e., $SO_2$ and $O_2$, at the surface of the reference electrode is determined by the dissociation pressure of $K_2SO_4$ and the equilibrium pressure of entrapped gas and $K_2SO_4$, it is essential to maintain a fairly constant cell temperature and a gas leak-free region between the reference electrode and the environment for successful operation of this integral cell.

This sensor apparatus presents a simple and practical combined $SO_2/O_2$ sensor unit to monitor $SO_2$ and $O_2$ levels in flue gases.

We claim:

1. A solid electrolyte dual gas sensor for measuring two selected component gases of a monitored gas environment by generating electrical signals on the basis of a difference in the partial pressure between (a) the two selected component gases of the monitored gas environment at first and second monitor electrodes in contact with the monitored gas environment and solid electrolyte, and (b) corresponding component reference gases at reference electrode means in contact with a reference gas environment and solid electrolyte; comprising a single reference electrode surrounded by a first solid electrolyte and a separate second solid electrolyte and being isolated from the monitored gas environment, the reference electrode being physically contacted by both electrolytes, the first electrolyte being oxygen ion conductive, and the second electrolyte having a composition conductive to sodium or potassium ions, one monitor electrode contacting the first solid electrolyte and, the other monitor electrode contacting the second solid electrolyte, where the second solid electrolyte is a single component composition disposed within a separate, ceramic oxide, interconnected skeletal matrix having a melting point greater than 1,600° C. and pores therein having approximate diameters of up to 150 micrometers, which is 35% to 95% porous prior to electrolyte impregnation, which matrix contains continuous interconnected pores filled with the second solid electrolyte, allowing a continuous ionic conduction path through the second solid electrolyte within the matrix, which second solid electrolyte is adapted upon heating to dissociate and provide the sole source of constant partial pressures of self-generated reference gases, at the reference electrode corresponding to the selected component gases to be measured in the monitored gas environment, to provide a unitary, dual gas sensor.

2. The solid electrolyte dual gas sensor of claim 1, where the electrodes are platinum electrodes that are attached to circuit means which are effective to generate an electrical signal measurement of the selected gas components in the monitored gas environment.

3. The solid electrolyte dual gas sensor of claim 2, where a first electrical circuit connects the reference electrode to the monitor electrode in contact with the second solid electrolyte, and a second electrical circuit connects the reference electrode to the monitor electrode in contact with the first solid electrolyte, said second circuit containing circuit shorting means.

4. The solid electrolyte dual gas sensor of claim 3, where the first solid electrolyte comprises zirconia and the second solid electrolyte is selected from one of the group consisting of $K_2SO_4$, $Na_2SO_4$, $K_2CO_3$, $Na_2CO_3$, $KNO_3$ and $NaNO_3$.

5. The solid electrolyte gas sensor of claim 1, where the ceramic oxide matrix is selected from the group consisting of quartz, alumina, zirconia, magnesia, and mullite.

6. The solid electrolyte dual gas sensor of claim 1, where a stable and constant partial pressure of the self-generated gases are maintained at the reference electrode.

7. The solid electrolyte dual gas sensor of claim 1, having platinum electrodes and operated at a temperature below the melting point of any of the solid electrolytes used in the sensor.

8. The solid electrolyte dual gas sensor of claim 1, where the second solid electrolyte is selected from one of the group consisting of $K_2SO_4$ and $Na_2SO_4$, and the selected gas components present in the monitored gas environment are $SO_2$ and $O_2$.

9. The solid electrolyte dual gas sensor of claim 1, where the first and second monitor electrode physically contact different bodies of electrolyte, and the first electrolyte provides a container for the reference electrode means.

10. The solid electrolyte dual gas sensor of claim 1, where the matrix material is from 50% to 95% porous, has a large void volume, a large surface area and pores having approximate diameters from 0.1 micrometer to 100 micrometers, and is in the form of a frit disc made from finely powdered particles, and where the second, solid electrolyte is melt impregnated into the matrix.

* * * * *